United States Patent
Seuthe

(10) Patent No.: US 10,288,586 B2
(45) Date of Patent: May 14, 2019

(54) COUPLING ELEMENT FOR ACOUSTICALLY COUPLING A SOUND TRANSDUCER TO A BODY, AND SOUND TRANSDUCER COMPRISING SAID COUPLING ELEMENT

(76) Inventor: Ulrich Seuthe, Wetter (DE)

(*) Notice: Subject to any disclaimer, the term of this patent is extended or adjusted under 35 U.S.C. 154(b) by 372 days.

(21) Appl. No.: 13/505,139

(22) PCT Filed: Nov. 2, 2010

(86) PCT No.: PCT/EP2010/006657
§ 371 (c)(1),
(2), (4) Date: Jun. 12, 2012

(87) PCT Pub. No.: WO2011/050991
PCT Pub. Date: May 5, 2011

(65) Prior Publication Data
US 2012/0250465 A1    Oct. 4, 2012

(30) Foreign Application Priority Data
Nov. 2, 2009 (DE) .................... 20 2009 014 771 U

(51) Int. Cl.
*G10K 11/00* (2006.01)
*G01N 29/28* (2006.01)
*G10K 11/02* (2006.01)

(52) U.S. Cl.
CPC ............. *G01N 29/28* (2013.01); *G10K 11/02* (2013.01); *G01N 2291/2638* (2013.01)

(58) Field of Classification Search
USPC .......................................... 367/14
See application file for complete search history.

(56) References Cited

U.S. PATENT DOCUMENTS

| | | | |
|---|---|---|---|
| 2,913,602 A | 11/1959 | Ivan | |
| 3,663,842 A | 5/1972 | Miller | |
| 5,426,980 A | 6/1995 | Smith | |
| 5,436,873 A * | 7/1995 | MacLauchlan et al. | 367/140 |
| 5,608,691 A * | 3/1997 | MacLauchlan et al. | 367/140 |
| 5,811,682 A * | 9/1998 | Ohtani et al. | 73/643 |
| 7,842,077 B2 * | 11/2010 | Hojeibane | 623/1.15 |
| 2004/0172126 A1* | 9/2004 | Hojeibane | 623/1.15 |
| 2009/0178484 A1* | 7/2009 | Kroning et al. | 73/598 |
| 2009/0217764 A1* | 9/2009 | Kroning et al. | 73/628 |
| 2012/0036934 A1* | 2/2012 | Kroning et al. | 73/628 |

FOREIGN PATENT DOCUMENTS

| | | |
|---|---|---|
| DE | 3814367 | 12/1988 |
| DE | 94 03 901 | 8/1994 |
| DE | 10 2006 023 716 | 12/2007 |

(Continued)

OTHER PUBLICATIONS

English Translation of Internation Search Report for PCT/EP2010/006657.*

*Primary Examiner* — James R Hulka
(74) *Attorney, Agent, or Firm* — Fay Sharpe LLP

(57) ABSTRACT

The invention relates to a coupling element for acoustically coupling a sound transducer to a body for transmitting high-frequency structure-borne noise from the sound transducer to the body and/or from the body to the sound transducer, wherein the coupling element includes a deformable contact region for positively contacting the body.

37 Claims, 3 Drawing Sheets

(56) References Cited

FOREIGN PATENT DOCUMENTS

| | | |
|---|---|---|
| DE | 102006059413 | 6/2008 |
| EP | 0095619 | 7/1982 |
| EP | 0 937 442 | 8/1999 |
| JP | 08021 828 | 1/1996 |
| JP | 20063 49 486 | 12/2006 |

\* cited by examiner

COUPLING ELEMENT FOR ACOUSTICALLY COUPLING A SOUND TRANSDUCER TO A BODY, AND SOUND TRANSDUCER COMPRISING SAID COUPLING ELEMENT

FIELD OF THE INVENTION

The invention relates to a coupling element for acoustically coupling a sound transducer to a body for transmitting high-frequency structure-borne noise from the sound transducer to the body and/or from the body to the sound transducer. According to this, the coupling element is provided for the acoustic coupling of a sound transducer to a body. In addition, the invention relates to a sound transducer for detecting and/or producing high-frequency structure-borne noise during the mechanical treatment of workpieces. According to this, the sound transducer is used to detect and/or produce high-frequency structure-borne noise from the sound transducer during the mechanical treatment of workpieces.

TECHNICAL BACKGROUND

The mechanical treatment of workpieces by means of, for example, cutting tools can be monitored by detecting structure-borne noise produced during the treatment in order to detect defects occurring during the treatment of the workpiece such as possibly crack formation in the workpiece or a tool fracture.

Such monitoring of the state or fracture of a tool or workpiece is known from DE 10 2006 023 716 B3. There a sound sensor is brought to rest flat against each of the two flat faces of a workpiece to be monitored. A drill fracture, for example, can be determined on the basis of a measurement of the difference between the transit times of sound signals to the two sound sensors. Here however, no particular requirements are imposed on the coupling of the sound sensor to the workpiece since merely the presence of a sound signal needs to be identified.

If the workpiece does not have any facilities for flat coupling for the sound sensor but rounded sections, a coupling element in the form of a scanning arm according to DE 94 03 901 U1 can be used for the point-by-point coupling of the sound sensor to the workpiece. A disadvantage here, however, is that the contact area of the sound sensor on the surface of the workpiece is small. This has the result that only a low acoustic power is transmitted from the workpiece to the sound sensor whilst the predominant fraction of the structure-borne noise power available for the evaluation remains unused.

In addition to the low transmitted acoustic power, however, the transmitted sound spectrum is limited in the case of merely point-by-point coupling and in DE 94 03 901 U1 is additionally possibly beset and falsified by interference signals due to a grinding contact.

Such a known point-by-point coupling is therefore not suitable for methods in which the sound emission spectrum overall is detected and evaluated. In particular when detecting the sound emission spectrum right up to very high frequency ranges, a merely point-by-point coupling proves to be unsuitable. A flat coupling of a sound sensor to round or stepped workpieces is, however, frequently impossible since the contact surfaces are not complementary.

An apparatus for non-destructive examination of test specimens using low-frequency sound signals is known from DE 10 2006 059 413 A1. An ultrasound transducer for low-frequency sound signals having a flexible membrane is known from U.S. Pat. No. 5,426,980 A. JP 08-0 21 828 A describes the use of cavities in a waveguide for damping sound waves. JP 2006-3 49 486 A discloses a sound sensor having a contact surface which is shaped complementary to the contact surface to be coupled.

Against this background, it is the object of the invention to provide a coupling element for acoustically coupling a sound transducer to a body for transmitting high-frequency structure-borne noise from the sound transducer to the body and/or from the body to the sound transducer and a sound transducer for detecting and/or producing high-frequency structure-borne noise during the mechanical treatment of workpieces by which means improved transmission of sound between a body on the one hand such as a mechanically treated workpiece or a tool and a sound sensor on the other hand is achieved.

DESCRIPTION OF THE INVENTION

This object is solved by a coupling element for the acoustic coupling of a sound transducer to a body and by a sound transducer.

According to this, the coupling element is deformable, at least in certain sections, whereby it can be brought in contact substantially positively with the body. The sensitive area of a sound transducer is thus adapted to arbitrarily shaped surfaces, e.g. to rounded sections, corners, steps, edges, protruding components and the like. A particularly good coupling is achieved in particular if the sound transducer together with the coupling element is pressed with a force against the body. The deformable coupling element nestles against the surface of the body. In this way, the largest possible contact area is formed. As a result of the large contact area between body and coupling element and therefore also between body and sound transducer, it is possible to transmit a comparatively high acoustic power from the body via the coupling element to the sound transducer. The energy yield of the sound pick-up is considerably increased by the coupling element according to the invention, for example, compared to scanning arms, in particular those having a tip and therefore small contact area. In addition, a large and in particular high-frequency sound spectrum for an acoustic frequency evaluation can be transmitted substantially unfalsified and in a broadband manner. Such an in particular broadband acoustic frequency evaluation using an acoustic emission spectrum up to high, preferably very high frequencies such as possibly in the high MHz range, enables a significantly improved process monitoring compared with other techniques.

Such sound can preferably be transmitted by the coupling element from the sound transducer to the body and/or from the body to the sound transducer, which sound is produced during the mechanical treatment of the in particular one workpiece or one body assigned to the workpiece. This sound is formed from high-frequency structure-borne noise. The evaluation of this high-frequency structure-borne noise spectrum provides information on the quality of the workpiece treatment. As a result of the deformability of the coupling element according to the invention, at least in certain areas, structure-borne noise signals from workpieces or tools having arbitrarily shaped surfaces can be evaluated with a comparatively high transmission of the acoustic power.

The coupling element preferably comprises a filling, which is surrounded at least in some sections by a sheath where the sheath is deformable. It is expedient if the filling is also deformable. Filling and sheath can thereby form a bag-like container. This container should be constituted so that structure-borne noise signals are transmitted as far as possible in a broadband manner and in particular including the high-frequency section of the spectrum sufficiently strongly and preferably unfalsified.

In a preferred embodiment of the coupling element according to the invention, it can be provided that the sheath is plastically or elastically deformable. Particularly suitable for the sheath in this case is a stretchable material by which means a comparatively good adaptation to the arbitrarily shaped surface of the body or the workpiece can be achieved. In the case of elastic deformability, the coupling element can be adapted particularly well to differently shaped bodies. In this way, sound signals of different workpieces can be detected with high efficiency. This is particularly advantageous in the industrial production of metal workpieces, for example, insofar as different workpieces each having differently shaped surfaces are to be manufactured there in different cycles.

The sheath of the filling of the coupling element according to the invention can be formed as desired from a film, a net, a textile or as desired from any combination thereof. The film is preferably formed from a plastic having elastic properties. The sound transmission behaviour of the film should be constituted so that high-frequency sound is transmitted at least partially. In addition, the film should satisfy the requirements of the workpiece treatment process, where in particular temperature and chemical resistance requirements need to be taken into account. Furthermore, the layer thickness of the film should also be adapted to the requirements for the degree of plastic or elastic deformability. A sheath of the filling formed from a net alternatively offers the advantage that the filling is not acoustically insulated from the surroundings. When the sheath is designed as a net, it is possible that the content of the net has direct contact with the body or the workpiece and/or the housing of the sound transducer. This direct contact of the filling improves the sound transmission. A sheath formed from a textile is characterised both by high deformability and also by high mechanical loading capacity and stressability.

It is particularly advantageous if the filling comprises transmission bodies which are at least partially in contact with one another at least in the state when placed or pressed against the body to be monitored in such a manner that they form one or more sound transmission paths between sound transducer and body. Such transmission bodies are advantageously formed from a solid material. This can, for example, comprise metal spheres, a granular material or the like. It is essential that the propagation of sound in the solid at high frequencies is significantly better than in those materials which do not have a solid state of aggregation. This applies, for example, to many metals. They are also characterised by a transmission of a higher bandwidth of acoustic frequencies where transmission bodies formed from solid materials also transmit the high-frequency component in the acoustic spectrum. If the speeds of sound in the transmission bodies are identical or at least similar to those in the body (workpiece, tool, machine, frame etc.) and/or in the sound transducer, then any reflection losses are significantly lower than when sound is coupled to liquid or gas. In the case of geometrically irregularly shaped transmission bodies, the interpretation of the sound data, in particular the sound reflections at the interfaces of the transmission bodies, can be complex. In order to simplify the interpretation of the sound data, it can therefore be appropriate if all the transmission bodies contained in the filling have a uniform geometry and are formed from the same material. If many small transmission bodies are provided, many parallel sound transmission paths which transmit a broadband acoustic spectrum are formed between the body and the sound transducer due to the contacts of the transmission bodies among one another.

In order to improve the sound transmission, it can be advantageous if the transmission bodies are not acoustically insulated by the sheath from the sound transducer but directly contact the sound contact surface thereof. It therefore proves to be expedient if the sheath has at least one opening so that the transmission bodies in the filling can be directly contacted with a section of the sound transducer. The filling is accordingly delimited on the one hand by the sheath and on the other hand by at least one region of the surface of the section of the sound transducer facing the coupling element. This section can, for example, be formed by the sensor surface itself or by a region of the housing in the vicinity of the sensor surface. The crucial thing is that in the region of the sound transducer, the transmission bodies can be directly in contact with the sensor surface without any acoustic insulation being formed by the sheath between the sensor surface and the transmission bodies.

The transmission bodies can advantageously be formed substantially spherical and/or polyhedral. These shapes of the transmission bodies which can preferably be metal or ceramic or be formed from another very hard material, lead to a high spatial filling of the coupling element according to the invention with both solid materials for transmission of the high-frequency fraction of the acoustic spectrum and having the property of deformability of the coupling element for adaptation to arbitrarily shaped surfaces. With spheres or polyhedra of identical dimensions and identical material, the sound reflection at the spherical surfaces can be filtered out more easily from the sound data during the data processing. When pressing a sound transducer having a coupling element according to the invention against a body such as, for example, a workpiece or a tool, the spheres and/or polyhedra are displaced inside the filling of the coupling element until they occupy a stable position in which as many transmission bodies as possible are acoustically contacted amongst one another. The sound is thus transmitted from the body or the workpiece or tool via the (metal) transmission bodies in contact with one another to the sensor surface or to the housing of the sensor. If there is a deviation from the spherical shape of the transmission bodies, the spatial filling of the coupling element can indeed be optimised but the (plastic) deformability of the filling can thereby be impaired; polyhedra however allow an increased force for producing a non-positive connection since the transverse forces and therefore the lateral pressure on the sheath are lower than in the case of spheres. The higher the spatial filling with spheres or similarly shaped transmission bodies, the better is the entire sound transmission of the coupling element. Any sound transmission losses are dependent on the condition of the sheath of the filling, in particular its thickness or strength, and on the total volume of the intermediate spaces between the spheres or the transmission bodies.

In addition, it can be expedient if the filling comprises a liquid. The liquid should preferably have a high viscosity, which is the case, for example, with an oil. If desired, the filling can also comprises a low-viscosity fat. A filling comprising both a liquid or a fat and also transmission bodies is particularly advantageous. The transmission bodies are thereby surrounded by the liquid or by the fat. The liquid in this case preferably transmits the low-frequency part of the sound spectrum. Alternatively a gel or a gel-like substance can also be applied as a component of the filling. This gel is characterised by the property of deformability. It is used as a (carrier) medium for the transmission bodies. If the filling comprises a liquid, the pressure of the liquid in the filling of the coupling element should be selected so that a displacement of transmission bodies contained therein is possible. When pressing the coupling elements onto the body, the pressure of the liquid can vary but is limited by the hydraulic properties of the liquid.

It can be provided that the filling comprises one or more voids. The presence of voids enables a better adaptation of the surface of the sheath to the free formed surface of the body of the workpiece. The variability of the deformable coupling element is thereby increased. If desired, the void can be filled with a gas.

The subject matter of the invention is also a sound transducer, in particular for detecting and/or producing preferably high-frequency structure-borne noise during the mechanical treatment of workpieces. The sound transducer comprises a sound sensor and/or a sound generator, and expediently a housing. According to the invention, a coupling element is disposed on the sound transducer, which is deformable at least in certain areas, whereby it can contact the body substantially positively. This coupling element can be characterised by one or more of the previously described features. The body whose sound is to be detected, can be formed by a tool or a workpiece or be acoustically coupled to this, e.g. a workpiece holder. In particular, this body can have free-formed surfaces, for example, concave or convexly formed surfaces or profilings on the surface. Due to the deformability of the coupling element of the sound transducer according to the invention, the contact region between free formed surface of the body and sensor surface of the sound transducer is increased. It is therefore possible to transmit a higher acoustic power from the body to the sound transducer or from the sound transducer to the body in particular in a broadband manner. In particular the interpretation of the structure-borne noise during a workpiece treatment is thereby more efficient with the result that the workpiece treatment is ultimately more reliable and higher-quality. This is all the more so in that due to the increase in the transmitted acoustic power, weak acoustic signals can also be detected which can be ascribed to a correspondingly weak anomaly in the workpiece treatment. This can, for example, comprise the formation of very fine cracks.

The sound sensor and/or sound generator preferably has a housing to which the coupling element is fastened. Coupling element and sound transducer thus form an apparatus unit.

The coupling element can further comprise a connecting piece to which the housing can be fastened. The connecting piece is preferably formed from a metal, in particular from the same metal from which essential components of the coupling element and the housing are formed. Metal is characterised by particularly good acoustic conductivity in the high-frequency part of the (structure-borne) noise spectrum.

The connecting piece can preferably be connected to the housing by means of a positive, a non-positive and/or a seamless connection. The connecting piece can, for example, be screwed to the sound sensor housing. Alternatively to this, it can also be plugged. The configuration of the sound transducer according to the invention with a screwable or pluggable connecting piece makes it possible to remove the coupling element from the sound transducer if required. Thus, for example, if the surface of the workpiece is planar-shaped, the sound transducer without coupling element can be placed directly on the workpiece with its likewise planar-shaped sensor surface. If workpieces having free-formed surfaces are then treated following the treatment of this workpiece with planar surface, the sound transducer can be used if required with the coupling element according to the invention by connecting to the connecting piece. In particular cases, it can also be expedient if the coupling element is adhesively bonded on the sound sensor housing or the sound generator housing. Such a connection is characterised in that it is particularly robust. In particular, with frequent changes of workpiece, the coupling element according to the invention cannot accidentally get lost.

Alternatively a connection of the connecting piece can be provided by a (permanent) magnetic interaction between connecting piece and sound transducer housing. In this case, the connecting piece comprises a permanent magnet or an electromagnet, whereby the connecting piece adheres to the magnetic sound sensor housing. The transmission bodies can also be permanently magnetic or magnetisable; a magnet can be attached below the sensor so that the force fit and/or form fit to the machine parts or the workpiece can be achieved by magnetic force through the coupling sack or out from this, which particularly facilitates the handling for manual adhesions and produces a reproducible pressing force.

In an advantageous embodiment of the sound transducer according to the invention, the sound sensor and/or the sound generator are formed from a piezoelectric component. Piezoelectric components are particularly well suited for sound transmission in the high-frequency range of the sound spectrum. Furthermore, the acoustic coupling of piezoelectric components to metal workpieces or metal components of the coupling element according to the invention is very suitable.

The aforesaid components which are described in the exemplary embodiments to be used according to the invention are not subjected to any particular exclusion conditions in their size, shape, choice of material and technical conception so that the known selection criteria in the area of application can be used restrictedly.

One non-limiting aspect of the present invention is directed to a coupling element for acoustically coupling a sound transducer to a body for transmitting high-frequency structure-borne noise from the sound transducer to the body and/or from the body to the sound transducer. The coupling element comprises a deformable contact region for positively contacting the body. The body can be a workpiece, which can be treated mechanically by a tool, or is acoustically coupled to the workpiece and/or the tool. The coupling element can include a filling, which is surrounded at least in some sections by a sheath, and wherein the sheath is deformable. The sheath can be plastically or elastically deformable. The sheath can be formed from a film, a net, and/or a textile. The filling can include transmission bodies, which can be brought at least partially in contact with one another and can form one or more sound transmission paths between the sound transducer and the body. The sheath can have an opening in the region whereof the transmission bodies are exposed for direct contact of a section of the sound transducer. The transmission bodies can be formed substantially spherical and/or polyhedral. The filling can include a liquid and/or at least one void. Another non-limiting aspect of the present invention is directed to a sound transducer, for detecting and/or producing high-frequency structure-borne noise during the mechanical treatment of workpieces. The sound transducer includes a sound sensor and/or a sound generator and the coupling element in accordance with the present invention. The housing of the sound transducer can be designed to receive the sound sensor and/or sound generator, and the coupling element is fastened to the housing. The coupling element has a connecting piece for acoustically coupled connection to the housing, where the connecting piece preferably is formed from a metal. The connecting piece can be connectable to the housing in an acoustically coupled manner by means of a positive, a non-positive and/or a seamless connection. The sound sensor and/or the sound generator can include a piezoelectric component.

Further details, features and advantages of the subject matter of the invention are obtained from the following description and the relevant drawings, in which, as an example, exemplary embodiments of a coupling element and a sound transducer are shown. Individual features of the embodiments can be combined with other features of other embodiments.

DETAILED DESCRIPTION OF EXEMPLARY EMBODIMENTS

Figure 1:
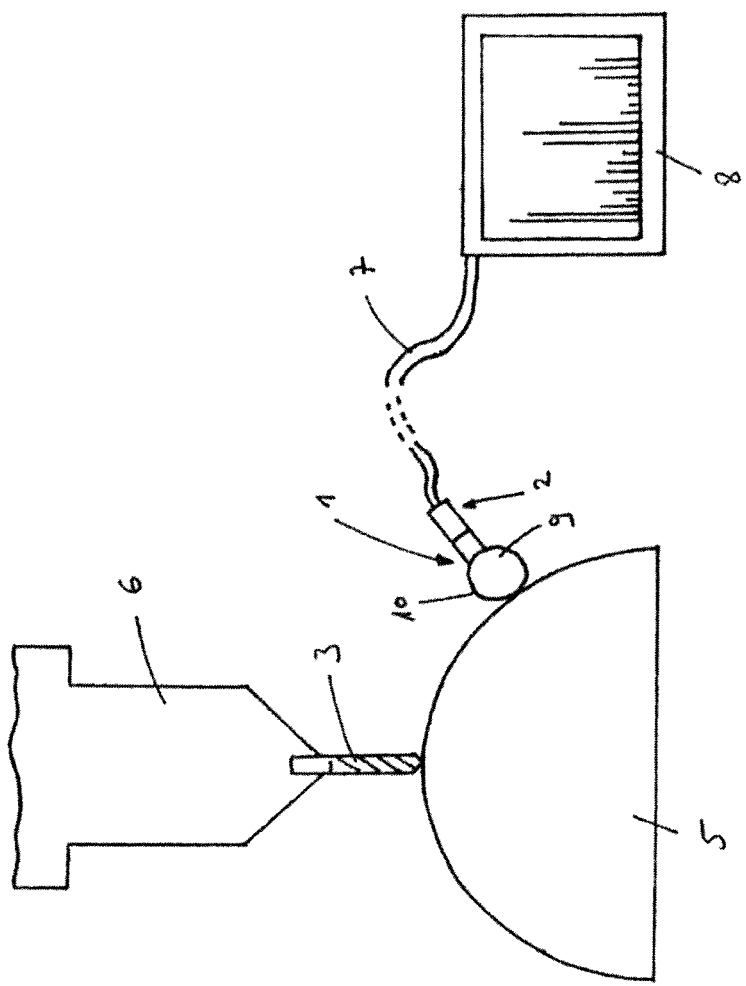
FIG. 1 illustrates schematically an apparatus for the treatment of a workpiece comprising a cutting tool, where means for receiving the structure-borne noise are provided on the workpiece.

FIG. 1 shows a tool treatment apparatus 6 in which a workpiece 5 is treated with a tool 3, here for example a drill. For monitoring the quality of the workpiece treatment a sound transducer 2 is attached to the workpiece 5, which is connected via a line 7 to an evaluation unit 8.

The structure-borne noise signals of the workpiece 5 which are generated during the treatment with the tool 3 are detected by the sound transducer 2 and evaluated in the evaluation unit 8. If a fracture or crack formation occurs during the workpiece treatment, this can be identified by interpretation of the acoustic signals in the evaluation unit 8. The possibility is therefore provided of separating out workpieces 5 in which a defect could be formed during the treatment thereof. The evaluation also makes further determinations possible such as, for example, conclusions on the state of wear of the tool etc. The quality of the workpiece treatment overall is improved by the monitoring. The sound transducer 2 can be coupled to the tool 6 or to a machine part acoustically coupled to the tool 6 and/or the workpiece 5 such as possibly a frame.

The workpiece 5 here for example has a spherical or convexly shaped surface. As a result of the convex surface, a sound transducer 2 whose sound sensor 14, cf. FIG. 2, has a planar sensor surface, can only be attached directly to the workpiece 5 in an unsatisfactory manner. The sound transducer 2 according to FIG. 1 therefore comprises a coupling element 1 which is deformable.

If the sound transducer 2 is now pressed with a force against the workpiece 5, the coupling element 1 becomes deformed and nestles against the curved surface of the workpiece 5. As a result, the contact area between the sound transducer 2 and the workpiece 5 is enlarged by the deformable coupling element 1 which can be adapted to the surface. As a result of the enlarged contact area, an overall higher acoustic power can be transmitted from the workpiece 5 to the sound transducer 2. Therefore weak acoustic signals can also be detected by the evaluation unit 8. Such weak acoustic signals are produced, for example, when a very fine crack is formed in the workpiece 5 during the processing by the tool 3.

The structure-borne noise emitted during the workpiece treatment predominantly comprises high-frequency acoustic frequencies. Alternatively to this, it can also be provided that the sound transducer 2 has a sound generator with which an acoustic signal is transmitted to the workpiece 5. This transmission of sound to the workpiece 5 can be used for example for direct monitoring of the tool treatment, on the other hand, the sound transducer 2 or the combination of workpiece 5 and sound transducer 2 can be calibrated by the transmitted sound.

Figure 2:
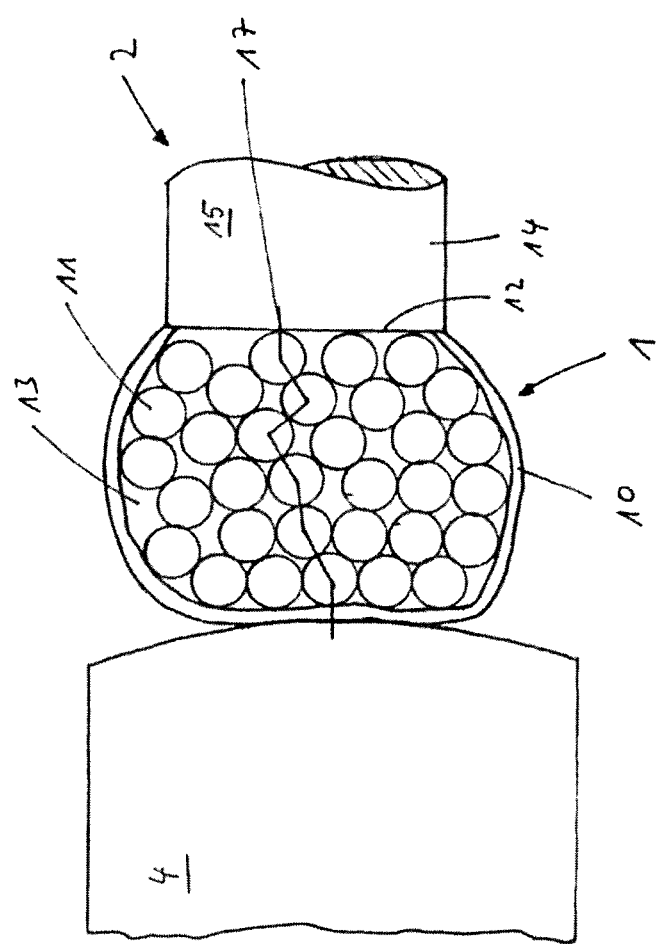
FIG. 2 illustrates schematically a coupling element disposed between a workpiece and a sound transducer and FIG. 3 illustrates schematically a sound transducer with a coupling element which is fastened to the sound transducer by means of a connecting piece.

A coupling element 1 for the acoustic coupling of a sound transducer 2 to a body 4 can be deduced from FIG. 2. Since the coupling element 1 is deformable at least in some areas, it can contact the body 4 substantially positively. It can be deduced from FIG. 2 that the coupling element 1 has a filling 9 which is surrounded at least in sections with a sheath 10. The sheath 10 is also deformable. The sheath 10 can preferably be plastically or elastically deformable. The sheath 10 can, for example, be formed from a film, net, a textile or a combination thereof. It can also be deduced from FIG. 2 that the filling 2 comprises transmission bodies 11 which are in contact with one another and form many parallel sound transmission paths 17 between body 4 and sound transducer 2, of which one is illustrated as an example. In this case, it is expedient that the sheath 10 has at least one opening 12. In the region of the opening 12 the transmission bodies 11 can be contacted directly with a section of the sound transducer 2. The sensor surface of the sound sensor 14 assigned to the sound transducer 2 can be located in the area of this section of the sound transducer 2.

According to FIG. 2, the transmission bodies are formed substantially spherical. It can be expedient if the spheres 11 are surrounded by a liquid. The liquid can, for example, comprise an oil. As desired or additionally, it can be expedient if the filling 9 comprises one or more voids 13. The configuration of the coupling element 1 with spheres which can preferably be formed of a metal and an oil surrounding the spheres affords the advantage that the coupling element 1 on the one hand can nestle very well against the free-formed surface of the body 4 and that on the other hand, both the low- and high-frequency fraction of the acoustic spectrum of the structure-borne noise can be transmitted from the body 4 via the spherical transmission bodies 11 directly to the sensor surface of the sound sensor 14 disposed in the sound transducer 2. At the same time, it can be identified that the housing of the sound transducer 2 is connected in one piece to the coupling element 1. The connection is configured in such a manner that the sheath 10 of the filling 9 of the coupling element 1 is applied directly to the housing of the sound transducer 2. In this case, an adhesive connection can be expedient. When manufactured in a precisely fitting manner, shrinking and an additional form fit with the aid of a groove is possible. In addition, a securing sleeve can be attached over the contact point, here screwing as with a clip, clamping, welding, soldering, adhesive bonding and/or the like is possible.

Figure 3:
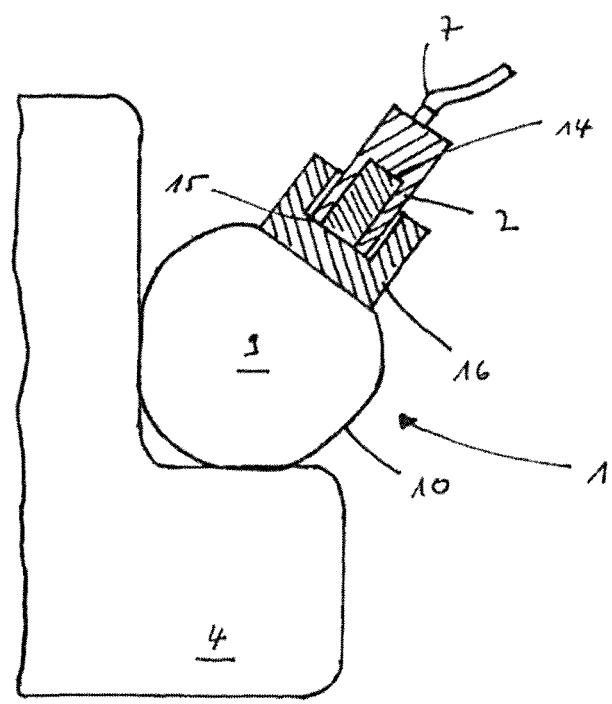

A sound transducer 2, in particular for the detection and/or generation of preferably high-frequency structure-borne noise during the mechanical treatment of workpieces can be deduced from FIG. 3. Accordingly the sound transducer also comprises a connecting piece 16 in addition to a sound sensor 14 and a housing 15. In addition to the sound sensor 14, a sound generator can also be provided, where the sound sensor 14 is expediently a combined sound sensor/sound generator. Sound sensor 14 and sound generator can be formed as a piezoelectric component. The connecting piece 16 forms a mechanical coupling between the coupling element 1 and the housing 15. It can be deduced from FIG. 3 that the connecting piece 16 can be screwed to the housing of the sound transducer 2. Alternatively to the screw connection, other connections can also be provided. As desired, these can be positive, non-positive or seamless. The connecting piece 16 is preferably formed of a metal. The configuration of the sound transducer according to the invention with a screwable connecting piece has the advantage that the coupling element 1 can be removed from the housing of the sound transducer 2 if required. It is therefore possible to apply the sound transducer 2 if desired directly, i.e. without coupling element, to the surface of the body 4 or the workpiece. In this case, the sensor surface or the housing 15 of the sound sensor 14 would be connected directly to the surface of the workpiece.

REFERENCE LIST

1 Coupling element
2 Sound transducer
3 Tool
4 Body
5 Workpiece
6 Workpiece treatment apparatus
7 Electrical connection
8 Evaluation unit
9 Filling
10 Sheath
11 Transmission body
12 Opening
13 Voids
14 Sound sensor
15 Housing
16 Connecting piece
17 Sound transmission path

The invention claimed is:

1. A coupling element for acoustically coupling a sound transducer to a body for transmitting high-frequency structure-borne noise from a) said sound transducer to said body, b) said body to said sound transducer, or combinations of a) and b), said coupling element including a deformable sheath that is plastically or elastically deformable, said deformable sheath having a deformable contact region for positively contacting the body, said coupling element comprising a filling which is at least partially surrounded by said deformable sheath, said filling comprising a plurality of transmission bodies which can form one or more sound transmission paths between said sound transducer and said body, a plurality of said transmission bodies are in contact with one another in said deformable sheath, a plurality of said transmission bodies are in direct contact with adjacently positioned transmission bodies to form a non-broken sound transmission path from a surface of said deformable sheath that is in contact with the body to said sound transducer, at least one of said plurality of said transmission bodies of said non-broken sound transmission path in contact with said sound transducer and another of said transmission bodies of said non-broken sound transmission path in contact with a portion of said deformable sheath that is in contact with the body when said deformable sheath is moved into contact with the body and all of said transmission bodies that form said non-broken sound transmission path are in direct contact with adjacently positioned transmission bodies that form said non-broken sound transmission path, said transmission bodies formed of a solid material, said transmission bodies having the same size and shape, said transmission bodies formed of the same material, said material of said transmission bodies is a metal material or a ceramic material, said transmission bodies having a shaped selected from the group consisting of spherical or polyhedral, said sheath having an opening such that a plurality of said transmission bodies are in direct contact with said sound transducer, said deformable sheath formed of a plastic material, a net material or a textile material.

2. The coupling element as defined in claim 1, wherein the body is a workpiece which can be treated mechanically by a tool, or said tool is acoustically coupled to said workpiece.

3. The coupling element as defined in claim 2, wherein said deformable sheath is formed from a net, said net having one or more openings that allows one or more of said transmission bodies to directly contact the body when said deformable sheath is pressed against the body.

4. The coupling element as defined in claim 3, wherein said filling includes a liquid, a gel, or combinations thereof.

5. The coupling element as defined in claim 4, wherein said coupling element forms a portion of a sound transducer, said sound transducer designed to detect high-frequency structure-borne noise during a mechanical treatment of workpieces, produce high-frequency structure-borne noise during the mechanical treatment of workpieces, or combinations thereof, said sound transducer including a sound sensor, a sound generator, or combinations thereof.

6. The coupling element as defined in claim 5, wherein a housing is provided for receiving said sound sensor, sound generator, or combinations thereof, said coupling element being fastened to said housing.

7. The coupling element as defined in claim 6, wherein said coupling element has a connecting piece for acoustically coupling said coupling element to said housing.

8. The coupling element as defined in claim 7, wherein said connecting piece includes a magnet.

9. The coupling element as defined in claim 8, wherein said connecting piece is connected in an acoustically coupled manner to said housing by means of a positive connection, a non-positive connection, a seamless connection, or combinations thereof.

10. The coupling element as defined in claim 9, wherein said sound sensor, said sound generator, or combinations thereof include a piezoelectric component.

11. The coupling element as defined in claim 10, wherein said transmission bodies are magnetic or magnetizable.

12. The coupling element as defined in claim 11, wherein a magnet connects said coupling element to said sound transducer, said magnet is located below said sound sensor, said sound generator, or combinations thereof.

13. The coupling element as defined in claim 12, wherein said deformable sheath has a generally spherical shape prior to being pressed against the body.

14. The coupling element as defined in claim 1, wherein said deformable sheath is formed from a net, said net having one or more openings that allows one or more of said transmission bodies to directly contact the body when said deformable sheath is pressed against the body.

15. The coupling element as defined in claim 1, wherein said filling includes a liquid, a gel, or combinations thereof.

16. The coupling element as defined in claim 1, wherein said coupling element forms a portion of a sound transducer, said sound transducer designed to detect high-frequency structure-borne noise during a mechanical treatment of workpieces, produce high-frequency structure-borne noise during the mechanical treatment of workpieces, or combinations thereof, said sound transducer including a sound sensor, a sound generator, or combinations thereof.

17. The coupling element as defined in claim 16, wherein a housing is provided for receiving said sound sensor, sound generator, or combinations thereof, said coupling element being fastened to said housing.

18. The coupling element as defined in claim 16, wherein said coupling element has a connecting piece for acoustically coupling said coupling element to said housing.

19. The coupling element as defined in claim 18, wherein said connecting piece includes a magnet.

20. The coupling element as defined in claim 18, wherein said connecting piece is connected in an acoustically coupled manner to said housing by means of a positive connection, a non-positive connection, a seamless connection, or combinations thereof.

21. The coupling element as defined in claim 16, wherein said sound sensor, said sound generator, or combinations thereof include a piezoelectric component.

22. The coupling element as defined in claim 1, wherein said transmission bodies are magnetic or magnetizable.

23. The coupling element as defined in claim 1, wherein a magnet connects said coupling element to said sound transducer.

24. The coupling element as defined in claim 1, wherein said deformable sheath has a generally spherical shape prior to being pressed against the body.

25. A sound transducer for detecting high-frequency structure-borne noise during a mechanical treatment of a workpiece, producing high-frequency structure-borne noise during said mechanical treatment of the workpiece, or combinations thereof, said sound transducer including a coupling element and one or more sound components selected from the group consisting of a sound sensor and a sound generator, said coupling element configured to acoustically couple said sound transducer to the workpiece for transmitting high-frequency structure-borne noise from a) said sound transducer to the workpiece, b) the workpiece to said sound transducer, or combinations of a) and b), said coupling element including a deformable sheath that is plastically or elastically deformable, said deformable sheath having a deformable contact region for positively contacting the workpiece, said coupling element comprising a filling which is at least partially surrounded by said deformable sheath, said filling comprising a plurality of transmission bodies which can form one or more sound transmission paths between said sound transducer and the workpiece, a plurality of said transmission bodies are in contact with one another in said deformable sheath, a plurality of said transmission bodies are in direct contact with adjacently positioned transmission bodies to form a non-broken sound transmission path from a surface of said deformable sheath that is in contact with the workpiece to said sound transducer, at least one of said plurality of said transmission bodies of said non-broken sound transmission path in contact with said sound transducer and another of said transmission bodies of non-broken sound transmission path in contact with a portion of said deformable sheath that is in contact with the body when said deformable sheath is moved into contact with the body and all of said transmission bodies that form said non-broken sound transmission path are in direct contact with adjacently positioned transmission bodies that form said non-broken sound transmission path, said transmission bodies formed of a solid material, said material of said transmission bodies is a metal material or a ceramic material, said transmission bodies having the same size and shape, said transmission bodies formed of the same material, said transmission bodies having a shaped selected from the group consisting of spherical or polyhedral, said deformable sheath formed of a plastic material, a net material or a textile material, said deformable sheath having an opening such that a plurality of said transmission bodies are in direct contact with said one or more sound components, said one or more sound components located in a housing, said one or more sound components include a piezoelectric component.

26. The sound transducer as defined in claim 25, wherein said sheath is formed from a net, said net having one or more openings that allows one or more of said transmission bodies to directly contact the workpiece when said deformable sheath is pressed against the workpiece.

27. The sound transducer as defined in claim 26, wherein said coupling element has a connecting piece for acoustically coupling said coupling element to said housing, said connecting piece includes a magnet to enable said coupling element to be releasably connected to said housing, said connecting piece is connected in an acoustically coupled manner to said housing by means of a magnetic connection.

28. The sound transducer as defined in claim 27, wherein said transmission bodies are magnetic or magnetizable.

29. The sound transducer as defined in claim 27, wherein said deformable sheath has a generally spherical shape prior to being pressed against the body.

30. The sound transducer as defined in claim 26, wherein said deformable sheath has a generally spherical shape prior to being pressed against the body.

31. The sound transducer as defined in claim 25, wherein said coupling element has a connecting piece for acoustically coupling said coupling element to said housing, said connecting piece includes a magnet to enable said coupling element to be releasably connected to said housing, said connecting piece is connected in an acoustically coupled manner to said housing by means of a magnetic connection.

32. The sound transducer as defined in claim 25, wherein said transmission bodies are magnetic or magnetizable.

33. The sound transducer as defined in claim 25, wherein said deformable sheath has a generally spherical shape prior to be pressed against the body.

34. The sound transducer as defined in claim 25, wherein said filling includes a liquid, a gel, or combinations thereof.

35. A sound transducer for detecting high-frequency structure-borne noise during a mechanical treatment of a workpieces, producing high-frequency structure-borne noise during said mechanical treatment of the workpieces, or combinations thereof, said sound transducer including a coupling element and one or more sound components selected from the group consisting of a sound sensor and a sound generator, said coupling element configured to acoustically couple said sound transducer to the workpiece for transmitting high-frequency structure-borne noise from a) said sound transducer to the workpiece, b) the workpiece to said sound transducer, or combinations of a) and b), said coupling element including a deformable sheath that is plastically or elastically deformable, said deformable sheath having a deformable contact region for positively contacting the workpiece, said coupling element comprising a filling which is at least partially surrounded by said deformable sheath, said filling comprising a plurality of transmission bodies which can form one or more non-broken sound transmission paths between said sound transducer and the workpiece, said transmission bodies formed of a solid material, at least one of said non-broken sound transmission paths formed of a plurality of said transmission bodies wherein a first end of said non-broken sound transmission path is formed of at least one of said transmission bodies being in contact with said deformable sheath and wherein a second end of said non-broken sound transmission path is formed of at least one of said transmission bodies being in contact with said sound transducer and wherein said transmission bodies that form said non-broken transmission path and which are positioned between said first and second ends of said sound transmission path are in direct contact with adjacently positioned transmission bodies that form said non-broken transmission path, said deformable sheath having an opening such that a plurality of said transmission bodies are in direct contact with said one or more sound components, said one or more sound components located in a housing.

36. The sound transducer as defined in claim 35, wherein said transmission bodies have the same size and shape, all of said transmission bodies are formed of the same material, all of said transmission bodies have a shaped selected from the group consisting of spherical or polyhedral, said deformable sheath formed of a plastic material, a net material or a textile material, said deformable sheath having an opening such that a plurality of said transmission bodies are in direct contact with said one or more sound components, said one or more sound components located in a housing, said one or more sound components include a piezoelectric component.

37. The sound transducer as defined in claim 36, wherein said deformable sheath is formed from a net, said net having one or more openings that allows one or more of said transmission bodies to directly contact the body when said deformable sheath is pressed against the body.

\* \* \* \* \*